United States Patent [19]

Prost et al.

[11] Patent Number: 4,663,330

[45] Date of Patent: May 5, 1987

[54] NOVEL DECAHYDROQUINOLINOL DERIVATIVES, AND PHARMACEUTICAL COMPOSITIONS AND METHODS USING THEM

[75] Inventors: Maurice Prost, Brussels, Belgium; Michel de Claviere, Saint Georges d'Orques, France; Peter Polster, Beauvechain, France

[73] Assignee: Sanofi, Paris, France

[21] Appl. No.: 744,213

[22] Filed: Jun. 13, 1985

[30] Foreign Application Priority Data

Jun. 13, 1984 [FR] France .................. 84 09242

[51] Int. Cl.$^4$ .................. A61K 31/47; C07D 215/22
[52] U.S. Cl. .................. 514/312; 546/153
[58] Field of Search .................. 546/153; 514/312

[56] References Cited

U.S. PATENT DOCUMENTS

| | | | |
|---|---|---|---|
| 3,882,129 | 5/1975 | Prost et al. | 546/153 |
| 4,173,636 | 11/1979 | Prost | 514/313 |
| 4,332,805 | 6/1982 | Prost et al. | 514/312 |
| 4,565,828 | 1/1986 | Descamps et al. | 514/469 |

FOREIGN PATENT DOCUMENTS

| | | |
|---|---|---|
| 0026168 | 4/1981 | European Pat. Off. . |
| 2257397 | 5/1973 | Fed. Rep. of Germany ...... 546/153 |
| 2160939 | 7/1973 | France . |

OTHER PUBLICATIONS

Prost, et al., Ann. Pharmaceutiques Francaises, vol. 43, No. 2, pp. 139–146 (09/85).
Prost, et al., Eur. J. Med. Chem.-Chimica Therapeutica, vol. 16, No. 2, pp. 119–123 (3–4/81).
J.A.M.A., vol. 247, No. 14, pp. 1911–1913, 1917 (04/09/82).
Prost, et al., Chemical Abstracts, vol. 80; 3398y (1974).
Prost, et al., Chemical Abstracts, vol. 95:24767t (1981).
Prost, et al., Chemical Abstracts, vol. 95:97612y (1981).
Prost, et al., Chemical Abstracts, vol. 104:224s (1986).
Search Report Of European Patent Application No. 85 870083.

*Primary Examiner*—Donald G. Daus
*Assistant Examiner*—Diana G. Rivers
*Attorney, Agent, or Firm*—Bacon & Thomas

[57] ABSTRACT

The invention relates to novel decahydroquinolinol derivatives represented by the general formula:

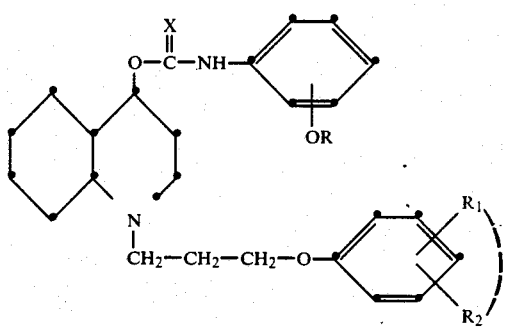

and pharmaceutically acceptable acid addition salts thereof, in which X represents oxygen or sulphur, R represents an alkyl radical having from 1 to 3 carbon atoms, $R_1$ represents fluorine, chlorine, bromine or methoxy, $R_2$ represents hydrogen or methoxy or $R_1$ and $R_2$, when they are taken together, represent a 2,3-methylenedioxy or 3,4-methylenedioxy radical.

The compounds of the invention are inhibitors of calcium translocation at the level of the cell membrane and are useful more particularly in the treatment of pathological syndromes of the cardiovascular system such as, for instance, angina pectoris.

18 Claims, No Drawings

NOVEL DECAHYDROQUINOLINOL DERIVATIVES, AND PHARMACEUTICAL COMPOSITIONS AND METHODS USING THEM

The present invention relates to novel heterocyclic compounds and more particularly to novel decahydroquinolinol derivatives as well as to a process for preparing them.

The decahydroquinolinol derivatives of the invention can be represented by the general formula:

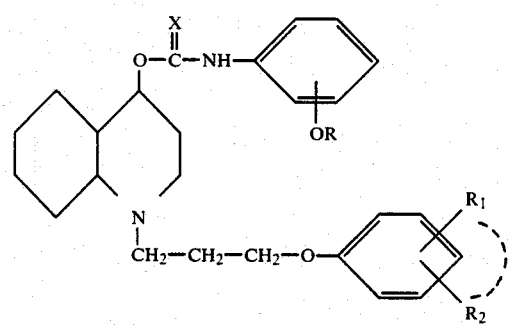

in which X represents oxygen or sulphur, R represents an alkyl radical having from 1 to 3 carbon atoms, $R_1$ represents fluorine, chlorine, bromine or methoxy, $R_2$ represents hydrogen or methoxy or $R_1$ and $R_2$ when they are taken together, represent a 2,3-methylenedioxy or 3,4-methylenedioxy radical.

Preferred compounds of the invention are those in which X represents sulphur.

The invention also relates to the pharmaceutically acceptable acid addition salts of the derivatives of formula I, for instance the hydrochloride.

The compounds of formula I possess in the 4-position of the decahydroquinoline ring a carbamoyloxy or thiocarbamoyloxy radical which can present an axial or equatorial configuration.

The invention relates to both the axial and equatorial epimers in question when taken individually or in the form of mixtures.

The decahydroquinolinol derivatives of the invention possess marked pharmacological properties. More particularly they are capable of inhibiting calcium translocation at the level of the cell membrane.

These properties are likely to render the compounds in question particularly useful in the treatment of certain pathological syndromes of the cardiovascular system.

Another object of the invention relates, therefore, to pharmaceutical or veterinary compositions containing as active ingredient, at least one decahydroquinolinol derivative in association with a pharmaceutical carrier or excipient therefor.

The invention also concerns a method of treatment of pathological syndromes of the cardiovascular system, comprising the administration to the subject needing such treatment of an effective dose of at least one decahydroquinolinol derivative of the invention.

Depending on the route of administration, the daily dosage for a human being weighing 60 kg will be from 2 to 500 mg of active ingredient.

The compounds of formula I can be prepared by reacting, at room-temperature, a N-substituted 4-hydroxy-trans-decahydroquinoline of general formula:

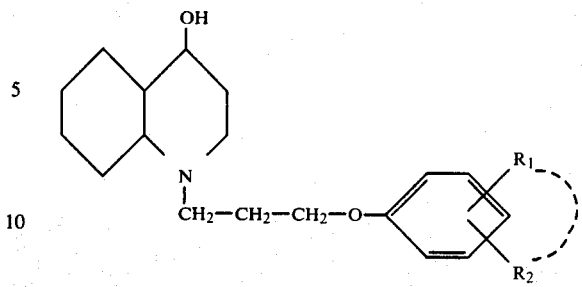

wherein $R_1$ and $R_2$ have the same meaning as above and in an inert organic solvent such as for example benzene, toluene, methylene chloride or chloroform, with a compound of general formula:

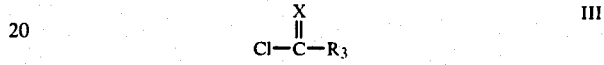

in which $R_3$ represents a chlorine atom or a phenoxy radical and X has the same meaning as above, to obtain a carbonyloxy or thiocarbonyloxy derivative of general formula:

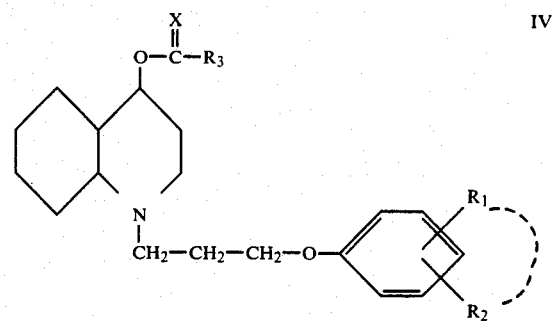

in which $R_1$, $R_2$, $R_3$ and X have the same meaning as above, which is condensed with a primary amine of general formula:

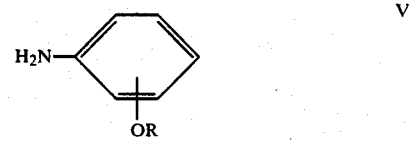

in which R has the same meaning as above, in an inert solvent and at room-temperature, to form the carbamic or thiocarbamic ester of formula I in free base form.

When $R_3$ represents a phenoxy radical, the reaction for obtaining a compound of formula IV is performed in the presence of a tertiary amine such as, for example, pyridine while the condensation of the compounds of formulae IV and V is carried out in an alcohol as solvent, for instance methanol.

When $R_3$ represents a chlorine atom, the condensation of the compounds of formulae IV and V is effected in a solvent such as, for example, toluene, methylene chloride or chloroform.

The pharmaceutically acceptable acid addition salts can be prepared, by classical procedure, by reacting the corresponding compound of formula I in free base form with an appropriate organic or inorganic acid.

The N-substituted 4-hydroxy-trans-decahydroquinoline of formula II can be obtained by the method described by M. PROST et al. in Eur. J. Med. Chem. 1981, 16, 119 or by other known procedures, for instance from 4-hydroxy-trans-decahydroquinoline and a halogenated compound of general formula:

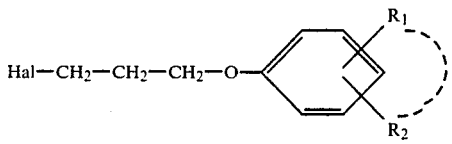

in which Hal represents a chlorine, bromine or iodine atom and $R_1$ and $R_2$ have the same meaning as above.

As regards the starting 4-hydroxy-trans-decahydroquinoline, this compound is also a known product which can be prepared by reducing 4-oxo-trans-decahydroquinoline following the method described, for instance, in Bull. Acad. Sci. U.S.S.R. 1962, 1599.

This method leads to a mixture of axial and equatorial epimers at the hydroxy level. These isomers, in separate form, have been described by M. PROST et al. in Eur. J. Med. Chem. 1976, 11 (4), pp. 337-342.

Therefore, the above-described processes for preparing the derivatives of formula I from 4-hydroxy-trans-decahydroquinoline can be applied either to the axial isomer or to the equatorial isomer of 4-hydroxy-trans-decahydroquinoline for the preparation of the corresponding epimers of formula I.

Similarly, the processes in question can also be applied to the mixture of axial and equatorial epimers of 4-hydroxy-trans-decahydroquinoline, obtained, for example, by reduction of 4-oxo-trans-decahydroquinoline with a view to preparing the compounds of formula I in the form of a mixture of axial and equatorial epimers.

4-Carbamoyloxy-trans-decahydroquinoline derivatives substituted on the carbamoyloxy, more particularly by a 4-methyl-phenyl radical, are described in European Pat. No. 0026168.

It has been found, within the framework the present invention, that compounds with structure similar to that of the above-cited known compounds but in which the 4-methyl-phenyl radical is replaced by an alkoxy-phenyl radical, more particularly a 4-methoxy-phenyl radical, are capable of inhibiting calcium translocation at the level of the cell membrane to a far higher degree than the prior-art (4-methyl-phenyl)-carbamoyloxy derivatives.

In some cases, the compounds of the invention were found to be more than ten times more active than one of the known compounds namely 4-[(4-methyl-phenyl)-carbamoyloxy]-1-[3-(4-fluoro-phenoxy)-propyl]-trans-decahydroquinoline (axial form).

These properties are capable of rendering the compounds in question very useful in the treatment of certain pathological syndromes of the cardiovascular system, more particularly in the treatment of angina pectoris, cardiac arrhythmia and hypertension.

Furthermore, the level of toxicity presented by the compounds of the invention is not such as to hinder their therapeutic use.

The inhibitory properties shown by the compounds of the invention with respect to calcium translocation at the level of the cellular membrane have been determined by measuring their antagonistic action with regard to the contractile response to potassium-induced depolarization on the isolated rat aorta (M. SPEDDING, Naunyn-Schmiedeberg's Arch. Pharmakol. 1982, 318, 234).

It is well known that depolarization by potassium of smooth-muscle membrane, renders the latter permeable to extracellular calcium and provokes muscular contraction.

Therefore, measuring the inhibition of te contractile response to potassium-induced depolarization or the tonic contraction to potassium-induced depolarization can constitute a means of evaluating the power of a compound to inhibit cellular membrane permeability to $Ca^{++}$ ions. The following technique was used:

The thoracic aorta of male rats of the Wistar species weighing out 300 g was removed and cut spirally in strips of about 40 mm long and 3 mm wide. These pieces were placed in a 25 ml-receptacle containing a modified Krebs-bicarbonate solution (NaCl 112 mM; KCl 5 mM; $NaHCO_3$ 25 mM; $KH_2PO_4$ 1 mM; $MgSO_4$ 1.2 mM; $CaCl_2$ 2.5 mM; glucose 11.5 mM; distilled water to 1000 ml). This solution was oxygenated while being maintained at 37° C.

The preparation was linked to an isometric force transducer and the contractile response was registered after being amplified.

A tension of 2 g was applied to the organ which was kept for 60 minutes in the modified Krebs-bicarbonate solution. Contractions were than provoked by replacing the Krebs-bicarbonate solution by a Krebs-potassium solution (NaCl 17 mM; KCl 100 mM; $NaHCO_3$ 25 mM; $KH_2PO_4$ 1 mM; $MgSO_4$ 1.2 mM; $CaCl_2$ 2.5 mM; glucose 11.5 mM; distilled water to 1000 ml). When the contractile response was found to be reproducible, a dose of $10^{-7}$ or $10^{-8}$ mol of a compound of the invention was introduced into the bath. Sixty minutes later, a new spasm was provoked by potassium depolarization.

The results obtained on each aorta studied were then expressed in % of the maximal contracting effect registered before incubation with the compound to be tested.

Examples of results so obtained are given below, the compounds of formula I being in axial and hydrochloride form.

| X | R | $R_1$ | $R_2$ | Maximal contracting effect (%) | |
|---|---|---|---|---|---|
| | | | | $10^{-7}$ M | $10^{-8}$ M |
| S | $CH_3$ | F | H | 25.6 | 85.8 |
| S | $CH_3$ | Br | H | 49.2 | |
| S | $CH_3$ | $OCH_3$ | H | 6.8 | 44.2 |
| S | $CH_3$ | $OCH_3$ | $OCH_3$ | 28.7 | 82.6 |
| S | $CH_3$ | O—$CH_2$—O | | 9.8 | 75.3 |

A comparative assay undertaken in the same conditions with 4-[(4-methyl-phenyl)-carbamoyloxy]-1-[3-(4-fluoro-phenoxy)-propyl]-trans-decahydroquinoline hydrochloride (axial form) has shown a maximal contracting effect of 74.3% at a dose of $10^{-7}$ mol.

It will be appreciated that for therapeutic use the compounds of the invention will normally be administered in the form of a pharmaceutical or veterinary composition, which may be in a dosage unit form appropriate to the desired mode of administration.

Thus, the pharmaceutical or veterinary composition may be in a dosage unit form suitable for oral administration, for example a coated or uncoated tablet, a hard- or soft-gelatin capsule, a packaged powder, a suspension or a syrup. The composition may alternatively take the form of a suppository for rectal administration or a sterile solution or suspension for parenteral administration.

When in dosage unit form, the compositions may contain, for example, from 15% to 50% of active ingredient by weight for oral administration, from 3% to 15% of active ingredient for rectal administration and from 3% to 5% of active ingredient for parenteral administration.

Irrespective of the form they may take, the pharmaceutical or veterinary compositions of the invention will normally be prepared by associating at least one of the compounds of formula I or a pharmaceutically acceptable acid addition salt thereof with an appropriate carrier or excipient therefor, for example one or more of the following substances: lactose, starches, talc, magnesium stearate, polyvinylpyrrolidone, alginic acid, colloidal silica, distilled water, benzyl alcohol or flavouring agents.

The following non-limitative Examples illustrate the invention:

EXAMPLE 1

1-[3-(4-Fluoro-phenoxy)-propyl]-4-[N-(4-methoxyphenyl)-thiocarbamoyloxy]-trans-decahydroquinoline hydrochloride (axial form).

A solution of 50 g of thiophosgene in 100 ml of methylene chloride was introduced between 0° and 5° C., into a solution of 40 g of 1-[3-(4-fluorophenoxy)-propyl]-4-hydroxy-trans-decahydroquinoline (axial form) in 300 ml of methylene chloride.

When the operation was terminated, the reaction mixture was maintained under stirring at a temperature of 20° to 22° C. for 3 days. The thiophosgene in excess was eliminated by means of a vacuum created by a water-pump while the temperature was maintained by mild heating at 20° to 25° C.

The volume was adjusted with methylene chloride, the reaction mixture was cooled to 0° to 10° C. and a solution of 60 g of 4-methoxy-aniline in 400 ml of methylene chloride was added.

When the operation was terminated, the reaction mixture was maintained for 3 days under stirring at a temperature of 20° to 22° C. and then water was added. After decantation, the organic phase was washed with 8 fractions each of 1 l of hydrochloric acid 1N. After drying and discolouring with active charcoal, the solvent was eliminated and the residue was allowed to crystallise in 150 ml of acetone.

In this manner, 24.3 g of 1-[3-(4-fluoro-phenoxy)-propyl]-4-[N-(4-methoxy-phenyl)-thiocarbamoyloxy]-trans-decahydroquinoline hydrochloride (axial form) were obtained.

Yield: 36.8%

M.P.: 220±1° C.

Starting from the appropriate products and using the process described above, the compounds hereunder were prepared:

1-[3-(4-Bromo-phenoxy)-propyl]-4-[N-(4-methoxyphenyl)-thiocarbamoyloxy]-trans-decahydroquinoline hydrochloride (axial form)

M.P.: 149±1° C. (ethyl acetate)

1-[3-(4-Methoxy-phenoxy)-propyl]-4-[N-(4-methoxyphenyl)-thiocarbamoyloxy]-trans-decahydroquinoline hydrochloride (axial form)

M.P.: 199±1° C. (ethyl acetate)

1-[3-(3,4-Dimethoxy-phenoxy)-propyl]-4-[N-(4-methoxy-phenyl)-thiocarbamoyloxy]-trans-decahydroquinoline hydrochloride (axial form)

M.P.: 188±1° C. (ethyl acetate)

4-[N-(4-Methoxy-phenyl)-thiocarbamoyloxy]-1-[3-(3,4-methylenedioxy-phenoxy)-propyl]-trans-decahydroquinoline hydrochloride (axial form)

M.P.: 204±1° C. (ethyl acetate)

EXAMPLE 2

1-[3-(4-Methoxy-phenoxy)-propyl]-4-[N-4-methoxyphenyl)-thiocarbamoyloxy]-trans-decahydroquinoline hydrochloride (axial form)

To a solution of 7.5 g of 4-hydroxy-1-[3-(4-methoxyphenoxy)-propyl]-trans-decahydroquinoline (axial form) in 50 ml of toluene and containing 4.5 ml of pyridine, was added, at a temperature of 5° to 10° C., a solution of 7 g of phenoxythiocarbonyle chloride in 30 ml of toluene.

When the operation was terminated, the reaction mixture was maintained for 3 days under stirring at a temperature of 20° to 22° C. The medium was then poured into 200 ml of a saturated sodium bicarbonate solution. After decantation, the aqueous phase was re-extracted with a toluene/ethyl ether mixture. The organic phases were collected, washed with water, dried and evaporated to dryness.

The residue was taken up in 50 ml of methanol and, at 0° to 5° C., this solution was added to a saturated solution of 4-methoxy aniline in methanol. When the operation was terminated, the reaction mixture was maintained under stirring at a temperature of 20° to 22° C. for 3 days. The medium was heated to 50°–60° C. and evaporated to dryness. The residue was then taken up in isopropanol. By adding a hydrochloric acid solution in isopropanol, the hydrochloride was formed. After evaporating to dryness, the salt was crystallised from a hexane/isopropanol mixture.

In this manner, 1-[3-(4-methoxy-phenoxy)-propyl]-4-[N-(4-methoxy-phenyl)-thiocarbamoyloxy]-trans-decahydroquinoline hydrochloride (axial form) was obtained.

Yield: 24%

M.P.: 199±1° C. (ethyl acetate)

EXAMPLE 3

In accordance with known pharmaceutical procedures, a soft-gelatin capsule was prepared by associating the following ingredients:

| Ingredient | mg |
| --- | --- |
| Compound of the invention | 100 |
| Corn starch | 384 |
| Talc | 10 |
| Colloidal silica | 6 |
| | 500 |

We claim:

1. A decahydroquinolinol compound of the the formula:

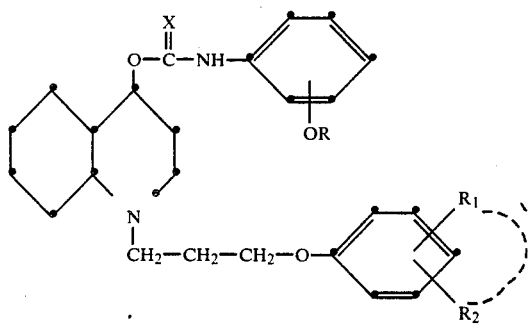

and pharmaceutically acceptable acid addition salts thereof, in which X is sulphur, R is an alkyl radical having from 1 to 3 carbon atoms, $R_1$ is fluorine, chlorine, bromine or methoxy, $R_2$ is hydrogen or methoxy or $R_1$ and $R_2$, when they are taken together, are a 2,3-methylenedioxy or 3,4-methylenedioxy radical.

2. A decahydroquinolinol compound according to claim 1, wherein the group —OR is in the 4-position.

3. A decahydroquinolinol compound according to claim 1 in the form of an axial epimer.

4. A decahydroquinolinol compound according to claim 1 in the form of an equatorial epimer.

5. The compound of claim 1 which is 1-[3-4-Fluoro-phenoxy)-propyl]-4-[N-(4-methoxy-phenyl)-thiocarbamoyloxy]-trans-decahydroquinoline (axial form) or a pharmaceutically acceptable acid addition salt thereof.

6. The compound of claim 1 which is 1-[3-(4-Bromo-phenoxy)-propyl]-4-[N-(4-methoxy-phenyl)-thiocarbamoyloxy]-trans-decahydroquinoline (axial form) or a pharmaceutically acceptable acid addition salt thereof.

7. The compound of claim 1 which is 1-[3-(4-Methoxy-phenoxy)-propyl]-4-[N-(4-methoxy-phenyl)-thiocarbamoyloxy]-trans-decahydroquinoline (axial form) or a pharmaceutically acceptable acid addition salt thereof.

8. The compound of claim 1 which is 1-[3-(3,4-Dimethoxy-phenoxy)-propyl]-4-[N-(4-methoxy-phenyl)-thiocarbamoyloxy]-trans-decahydroquinoline (axial form) or a pharmaceutically acceptable acid addition salt thereof.

9. The compound of claim 1 which is 4-[N-(4-Methoxy-phenyl)-thiocarbamoyloxy]-1-[3-(3,4-methylenedioxy)-phenoxy)-propyl]-trans-decahydroquinoline (axial form) or a pharmaceutically acceptable acid addition salts thereof.

10. A decahydroquinolinol compound according to claim 1 wherein the pharmaceutically acceptable acid addition salt is the hydrochloride.

11. A decahydroquinolinol compound according to claim 2 in the form of an axial epimer.

12. A decahydroquinolinol compound according to claim 2 in the form of an equatorial epimer.

13. A decahydroquinolinol compound according to claim 2, wherein the group R is methyl.

14. A decahydroquinolinol compound according to claim 11, wherein R is methyl.

15. A decahydroquinolinol compound as claimed in claim 12 wherein R is methyl.

16. A pharmaceutical or veterinary composition comprising, as active ingredient, at least one decahydroquinolinol compound according to claim 1, in association with a pharmaceutical carrier or excipient therefor.

17. A method for treating angina pectoris, cardiac arrhythmia and hypertension which comprises administering to a patient in need thereof an effective amount for treating angina pectoria, cardiac arrhythmia or hypertension of at least one decahydroquionolinol compound as claimed in claim 1.

18. A method according to claim 17 wherein the daily dosage for a human being is from 2 to 500 mg of active ingredient.

* * * * *